United States Patent [19]
Nash

[11] 3,972,121

[45] Aug. 3, 1976

[54] PRESSURE REDUCER FOR AIR DRIVEN DENTAL HANDPIECE

[76] Inventor: John E. Nash, 145 Oak St., Downingtown, Pa. 19335

[22] Filed: Aug. 12, 1974

[21] Appl. No.: 496,605

[52] U.S. Cl.................................. 32/27; 138/44
[51] Int. Cl.².................................. A61C 1/10
[58] Field of Search........... 138/44; 215/355; 32/26, 32/27

[56] References Cited
UNITED STATES PATENTS

| | | | |
|---|---|---|---|
| 1,567,043 | 12/1925 | Boeschevalier | 138/44 |
| 2,409,294 | 10/1946 | Martin | 138/44 |
| 2,577,780 | 12/1951 | Lockhart | 215/355 |
| 3,210,848 | 10/1965 | Bizzigotti | 32/27 |

*Primary Examiner*—Robert Peshock

[57] ABSTRACT

An air driven dental handpiece having means for securing a dental bur and means for supplying a rotative power to the dental bur. The power is supplied, in the preferred embodiment, by an air turbine. The handpiece includes an air supply conduit within the handle, with a conduit furnishing the air to supply the rotative power to the dental bur. The improvement comprises the insertion of a means for reducing the air pressure to the power supply means in order to have the handpiece run at a pressure which is lower than the dentist's line pressure, without the necessity of changing the line pressure.

2 Claims, 8 Drawing Figures

U.S. Patent Aug. 3, 1976 3,972,121
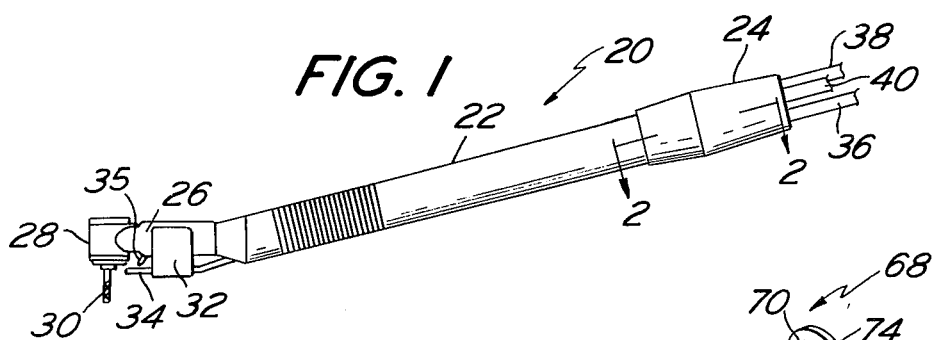
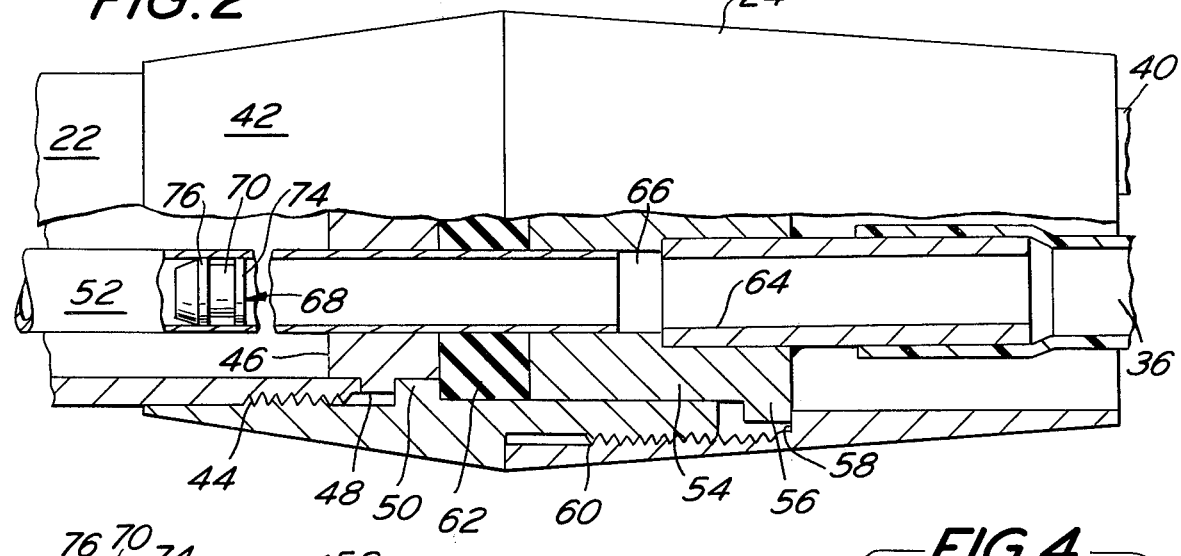
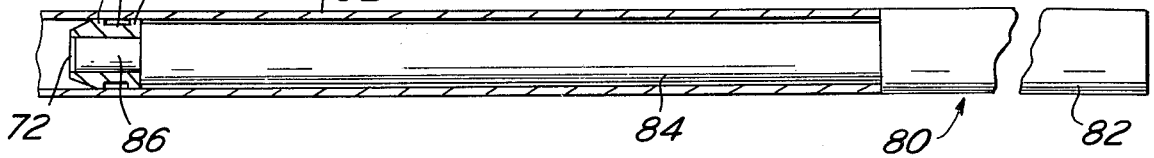
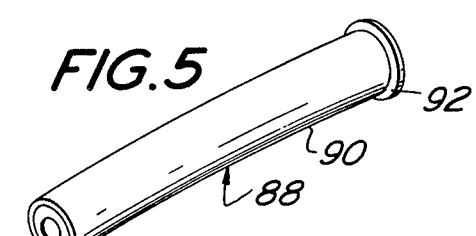
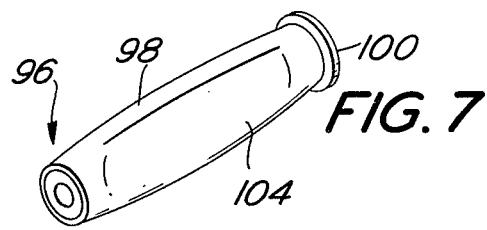
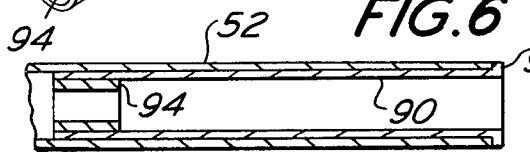
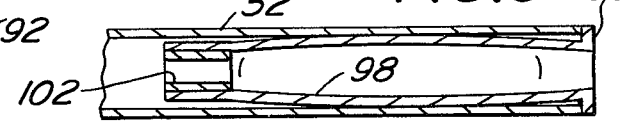

PRESSURE REDUCER FOR AIR DRIVEN DENTAL HANDPIECE

This invention relates to an air driven dental handpiece, and more particularly, to a pressure reducer used in the air driven dental handpiece.

It is now common practice in the dental art to supply rotative power to a dental handpiece through the use of an air driven rotor or turbine. In fact, many dentists use air power in connection with all of the power equipment used on a patient, such as a high speed, contra-angle air turbne handpiece, a low speed, high torque straight handpiece and a water-air syringe. In the past, all of the air driven equipment used by the dentist was designed to operate at the same line pressure, which is normally approximately 35 psi. Recently, however, contra-angle handpieces have been developed which have a much smaller air turbine. One such handpiece employing the smaller air turbine is disclosed in co-pending U.S. application Ser. No. 217,745, filed Jan. 14, 1972, the entire disclosure of which is incorporated by reference herein.

The smaller air turbines will operate at the normal line pressure utilized in a dentist's office. But it has been found that they will operate more effectively at lower pressure. Again, by way of example, although the normal line pressure in a dentist's office is 35 psi, the smaller air turbines will operate more effectively at an incoming pressure of approximately 25 psi, which in turn results in a pressure at the turbine of approximately 19 psi. When the smaller air turbines are operated at a line pressure of 35 psi, it has now been found that there is extensive wear on the bearings and other moving parts, to the extent that these parts will wear out in a much quicker time than would occur if a proper incoming pressure were used.

Dentists have been made aware of the problem of excessive air pressure on the smaller air turbines, and in an attempt to obviate the problem, they have reduced the line pressure for all of their dental equipment. Although this corrects the problem with air turbine handpiece, it creates a problem with the other air-powered equipment that the dentist uses, since these other pieces of equipment will then have to be operated at lower pressures than the optimum operating pressure. Therefore, the dentist is faced with the problem of continually adjusting the line pressure, or in the alternative, operating his air turbine handpiece at higher than the most effective pressure. The problem becomes particularly acute when the dentist must constantly shift from use of the air turbine to use of the chip blower or syringe. Accordingly, most dentists will leave their line pressure at approximately 35 psi, and operate the air turbine handpiece at higher than recommended and optimum pressures.

Having recognized the existence of this problem, the device of this invention is used to solve the problem. Thus, by this invention, a means is provided for reducing the incoming pressure to the handpiece to the maximum effective pressure. A device can be permanently installed within the handpiece, and the dentist need make no further adjustment, once the device is installed. No adjustment need be made to the line pressure, and accordingly all of the dental equipment can be run at the same line pressure. The device of this invention can be made in varying sizes in order to correct the pressure for any given incoming pressure.

It is accordingly an object of this invention to provide a dental handpiece having a pressure reducer therein.

It is a further object of this invention to provide a novel method of modifying any air driven dental handpiece to reduce the pressure of the air passing through the handpiece.

These and other objects of this invention are accomplished by providing an air driven dental handpiece comprising a handle, means for securing a dental bur within said handpiece, means for supplying rotative power to said dental bur, said power means being air-driven, conduit means within said handle for supplying air to said power means and means within said conduit means for reducing the pressure of the air reaching said power means, said pressure-reducing means comprising tubular means in said air conduit means, said tubular means having an internal diameter smaller than the internal diameter of said air conduit.

Other objects and many of the attendant advantages of this invention will be readily appreciated as the same becomes better understood by reference to the following detailed description when considered in connection with the accompanying drawings wherein:

FIG. 1 is a side elevational view of an air driven dental handpiece including the pressure reducer of this invention;

FIG. 2 is an enlarged, partial sectional view taken along the line 2—2 of FIG. 1;

FIG. 3 is a perspective view of a first embodiment of the pressure reducer of this invention;

FIG. 4 is a sectional view showing a tool for inserting the pressure reducer of FIG. 3 in the air conduit of the dental handpiece of FIG. 1;

FIG. 5 is a perspective view of a second embodiment of the pressure reducer of this invention;

FIG. 6 is a sectional view of the device of FIG. 5, as inserted in the air conduit of a dental handpiece;

FIG. 7 is a perspective view of a third embodiment of the pressure reducer of this invention; and FIG. 8 is a sectional view showing the embodiment of the pressure reducer of FIG. 7 in an air conduit of a dental handpiece.

Referring now in greater detail to the various figures of the drawings wherein like reference characters refer to like parts, an air driven dental handpiece including the pressure reducer of this invention is generally shown at 20 in FIG. 1. Device 20 basically comprises a handle 22 having a connector sleeve 24 secured at the rear thereof. Handle 22 includes angled neck 26 and a turbine housing 28 mounted perpendicularly to neck 26.

An air turbine is mounted within turbine housing 28 and a dental bur 30 is secured by a chucking mechanism within the air turbine. The dental handpiece also includes a collar 32 which is slidable on neck 26. Water spray tubes 34 are secured by the collar. The handpiece also includes an internal fiber optic system, which terminates in a pair of tubes containing the light transmitting fibers, with one of the tubes beng shown at 35 in FIG. 1.

The connector sleeve 24 is used for connecting the external sources of air, water and light with the handpiece. Thus, sleeve 24 houses the ends of air tube 36, water tube 38 and sleeve 40 containing the light transmitting glass fibers forming a part of the internal fiber optic system.

Referring to FIG. 2, it is seen that an adaptor nut 42 is threadedly secured on the rear of handle 22, as indicated at 44. A spacer 46 includes an annular lip 48 which abuts the rear of handle 44. Adaptor nut 42 includes an internal annular rib 50 which abuts lip 48 when the adaptor nut is threadedly secured in place. Accordingly, the spacer plate 46 is rigidly held in place by the adaptor nut.

A rigid air conduit 52 is secured in an opening within spacer 46 and projects therethrough. Similarly, a water conduit and a sleeve containing the fiber optic bundle also project through plate 46, although these additional elements are not shown.

A plug 54 is slidably mounted in the rear of adaptor nut 42. Plug 54 includes a rear annular rim 56. Connector sleeve 24 includes an annular shoulder 58 which abuts the rear of rim 56. The connector sleeve 24 is threadedly secured on adaptor nut 42, as shown at 60, and the abutment of shoulder 58 against rim 56 holds the plug 54 in place. A gasket 62, of compressible material such as rubber, is positioned between spacer plate 46 and plug 54.

A rigid tube 64 is secured in a channel 66 of plug 54. Inlet air tube 36, which is formed from flexible tubing, is secured on tube 64, and the incoming air passing through tube 36 continues its passage into air conduit 52 via channel 66. Suitable connections for the incoming water tube and fiber optic bundle are also made within adaptor nut 42.

To the extent described above, the handpiece 20 is identical to that disclosed and claimed in aforementioned U.S. application Ser. No. 217,745, filed Jan. 14, 1972. Additional details of the handpiece can be found in that application, the disclosure of which has been incorporated by reference herein. However, it should be understood that the pressure reducer of this invention is adapted for use in all air driven dental handpieces, and not just the handpiece described herein. By way of further non-limiting example, it can also be used in the handpiece disclosed in U.S. Pat. No. 3,120,706.

A first embodiment of the pressure reducer is generally shown at 68 in FIG. 3. Device 68 comprises a tube 70 having a hollow bore 72 of constant diameter. An annular flange 74 projects outwardly from tube 70 adjacent the rear thereof. A second flange 76 projects from tube 70 adjacent the front thereof. The front of flange 76 is frusto-conical and tapers downwardly towards the front of tube 70, as shown at 78.

Device 68 is metallic, and is preferably formed of brass. It can machined from a single piece of brass stock, or in the alternative, tube 70 can have flanges 74 and 76 secured thereon, as by a pressed fit. As seen in FIG. 2, device 68 is used by insertng the same in air conduit 52.

Referring now to FIG. 4, a device for inserting pressure reducer 68 is shown at 80. Device 80 includes a first cylindrical portion 82, a second cylindrical portion 84 and a third cylindrical portion 86. The diameter of cylindrical portion 82 is the same as the diameter of air conduit 52. The diameter of portion 84 is slightly less than the internal diameter of air conduit 52. The diameter of portion 86 is slightly less than the internal diameter of bore 72 of pressure reducer 68.

In use, the pressure reducer 68 is placed on cylindrical portion 86, with the rear flange 74 abutting the front of portion 84. The pressure reducer 68 is placed in conduit 52 and the inserter 80 is pushed forwardly within the conduit 52 until the rear edge of conduit 52 abuts the leading edge of cylindrical portion 82. At this point, the pressure reducer 68 is properly seated within the air conduit 52, and inserter 80 is removed by withdrawing it from the air conduit.

It is thus seen that device 68 effectively reduces the internal diameter of air conduit 52 down to any desired internal diameter. The reduction in the internal diameter of the air conduit in turn causes a reduction in the pressure of the air reaching the turbine, which is down stream from the pressure reducer. By way of example, if the pressure entering the air conduit 52 is 35 psi, through the use of an appropriate diameter for bore 72, the pressure leaving the reducer 68 will be 25 psi. Through the proper selection of diameters for pressure reducer 68, any desired downstream pressure for the air can be obtained. Thus, all that is required is that the internal diameter of the pressure reducer be less than the internal diameter of air conduit 52 to cause a reduction in the air pressure.

A second embodiment of a pressure reducer is generally shown at 88 in FIG. 5. Device 88 basically comprises a tube 90 having an annular flange 92 at its rear end. A tube 94 is inserted in the forward end of the tube 90. In this embodiment of the pressure reducer, as seen in FIG. 5, the tube 90 is slightly curved. This can be accomplished when the tube is formed.

The curved tube 90 is inserted in the rear end of air conduit 52. When insertion has been completed, the annular flange 92 abuts the rear edge of conduit 52. Since this device is inserted at the rear end of the air conduit, no special tool is needed for insertion. Although the tube 90 was originally curved, when it is placed in the air conduit 52, it is straightened. However, there is a residual tendency of the tube to curve, and this holds the tube rigidly in place.

Here again, it is seen that the pressure reduction in conduit 52 is accomplished by having the small tube 94 with the reduced diameter. Thus, the pressure of the air is reduced as it passes through the constriction formed by the reduced diameter of the pressure reducer. Again, any downstream pressure desired can be obtained by the judicious selection of an internal diameter for the tube 94.

A third embodiment of the pressure reducer of this invention is generally shown at 96 in FIG. 7. Here again, this device includes a tube 98 having an annular flange 100 at its rear end. A small tube 102 is inserted in the forward end of tube 98, and is held therein by a pressed fit. In this embodiment, the tube 98 is provided with a pair of flattened sides 104 (one shown in FIG. 7) which are formed by compressing the tube. The flattening of the sides 104 in turn causes the remainder of the tube to bulge. Accordingly, when the tube 98 is inserted in air conduit 52, the bulge portions are compressed, and this frictionally holds the tube 98 within the conduit 52. Here again, the reduced diameter of tube 102 causes a pressure drop in the air passing through the air conduit 52.

It is thus seen that various embodiments of pressure reducers have been provided by this invention. The one feature that all of them have in common is the fact that they provide a reduced diameter for the air conduit 52 within an air driven dental handpiece, and this in turn causes a pressure drop of the air passing through the pressure reducer. Embodiments 88 and 96 are insertable in the air conduit 52 at the rear, without the necessity of employing any auxiliary tools. Insofar as embodiment 68 is concerned, it is easily inserted utilizing the device shown at 80 in FIG. 4. One of the features of the devices shown at 88 and 96 is that they are readily removable in the event a dentist wishes to change the pressure reducer to change the pressure reaching the turbine of the handpiece, or in the event that the line pressure is increased or decreased. Thus, a series of pressure reducers can be provided, with each pressure reducer being adapted to change line pressure at a given pressure to a desired pressure.

The pressure reducers of this invention can be formed from any materials known to the art utilized in dental handpieces. Because of its softness and bendability, brass is preferred.

Having the frusto-conical front 78 in device 68 aids in the insertion of the device into the air conduit 52. Although the annular flanges 74 and 76 rigidly fit within conduit 52, the surface contact is sufficiently minimal to permit the forcing of the device 68 into the conduit by the inserting tool 80. However, there is sufficient surface contact to prevent the device 68 from being dislodged by the air passing through the conduit 52.

The device of this invention is adapted for use in all air driven dental handpieces. Its preferable use is in the handpiece shown, which utilizes a turbine that is smaller than that normally used in air driven dental handpieces. Although a water spray system and a fiber optic system have been shown, they form no part of this invention.

The primary advantage of this invention is that a dentist can adjust the air pressure of a single piece of equipment while maintaining the air pressure for all of the other pieces of equipment he utilizes. Where a dentist has only one piece of air operated equipment, he can adjust the pressure for that piece of equipment at its source. In this case, the pressure reducer will not be necessary. However, the pressure reducer of this invention will be needed by most dentists, since substantially all dentists have a number of pieces of equipment operating on air.

Without further elaboration, the foregoing will so fully illustrate my invention that others may, by applying current or future knowledge, readily adapt the same for use under various conditions of service.

I claim:

1. An air driven dental handpiece comprising a handle, means for securing a dental bur within said handpiece, means for supplying rotative power to said dental bur, said power supply means being air driven, conduit means within said handle for supplying air to said power supply means and means within said conduit means for reducing the pressure of the air reaching said power means, said pressure reducing means comprising tube means within said air conduit means, said tube means being frictionally engaged within said air conduit means, said tube means being slightly arcuate in shape and said conduit means being cylindrical, with said conduit means tending to straighten said tube means, thereby frictionally engaging said tube means in said air conduit means, said tube means having an internal diameter smaller than the internal diameter of said air conduit means, whereby air for driving said power supply means enters said conduit means at a first predetermined pressure and said air leaves said pressure reducing means at a second predetermined pressure, said second pressure being lower than said first pressure, and said second pressure being determined by the internal diameter of said tube means.

2. An air driven dental handpiece comprising a handle, means for securing a dental bur within said handpiece, means for supplying rotative power to said dental bur, said power supply means being air driven, conduit means within said handle for supplying air to said power supply means and means within said conduit means for reducing the pressure of the air reaching said power means, said pressure reducing means comprising tube means within said air conduit means, said tube means being frictionally engaged within said air conduit means, said tube means being crimped on its sides, thereby causing bulges at its top and bottom, said bulges being compressed by said air conduit means, whereby said tube means is frictionally held within said air conduit means, said tube means having an internal diameter smaller than the internal diameter of said air conduit means, whereby air for driving said power supply means enters said conduit means at a first predetermined pressure and said air leaves said pressure reducing means at a second predetermined pressure, said second pressure being lower than said first pressure, and said second pressure being determined by the internal diameter of said tube means.

\* \* \* \* \*